United States Patent
Strumor et al.

[19]

[11] Patent Number: 6,149,939
[45] Date of Patent: Nov. 21, 2000

[54] HEALTHFUL DISSOLVABLE ORAL TABLETS, AND MINI-BARS

[76] Inventors: Mathew A. Strumor, 158 Key Heights Dr., Tavernier, Fla. 33070; Judy S. Hartman, 130 Orion Cir., Jupiter, Fla. 33477

[21] Appl. No.: 09/174,674

[22] Filed: Oct. 19, 1998

Related U.S. Application Data

[63] Continuation-in-part of application No. 08/854,257, May 9, 1997, abandoned.

[51] Int. Cl.$^7$ ............................... A61K 9/20; A61K 9/28
[52] U.S. Cl. ..................... 424/464; 424/435; 424/439; 424/441; 424/474; 424/484
[58] Field of Search ..................... 424/464, 465, 424/484, 473, 469, 435, 439, 441, 474

[56] References Cited

U.S. PATENT DOCUMENTS

| | | | |
|---|---|---|---|
| 5,356,635 | 10/1994 | Raman et al. | 424/484 |
| 5,626,892 | 5/1997 | Kehoe et al. | 426/3 |

*Primary Examiner*—James M. Spear
*Attorney, Agent, or Firm*—Richard L Huff

[57] ABSTRACT

Dissolvable oral tablets and mini-bars which contain healthful ingredients. The products contain a multitude of discrete, extruded sections containing different healthful ingredients. A wide variety of active ingredients includes oxygen enhancers, vitamins, enzymes, dehydrated foods, pycnogenols, food supplements, soy proteins, herbs, roots, and mints. The tablets and mini-bars may be prepared by extruding discrete sections and matrix, all containing active ingredients, cutting the resulting shape for the tablet and mini-bar, and coating with dehydrated food. The tablets and mini-bars may supply needed active ingredients following natural disasters or prior to surgery or may be taken for general use. The products may be contained in a thermal insulating wrapper having an inner piece, an outer piece, and a corrugated piece between the inner and outer pieces. The products may be stored in a thermally insulating luminous canteen container having a primary container having a removable cover and a plurality of secondary containers affixed to the outer wall of the primary container, which containers have removable attached covers. The container may be constructed of hypoallergenic thermoplastic rubber, and may contain a compass and a signaling mirror. These containers also hold water and first aid supplies. The canteen containers may be supplied to survivors of natural disasters or used for general utility.

9 Claims, 8 Drawing Sheets

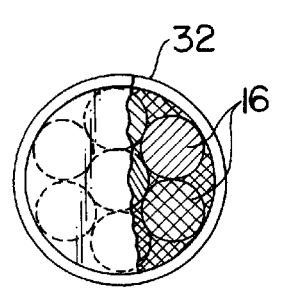
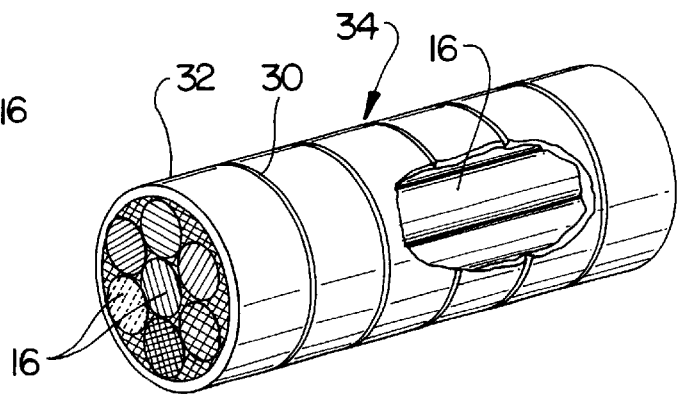
FIG. 7          FIG. 8
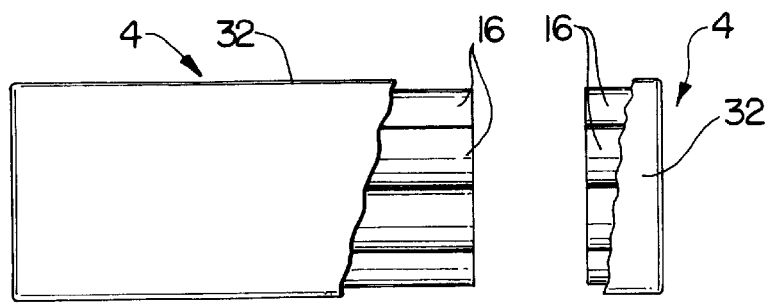
FIG. 9          FIG. 10
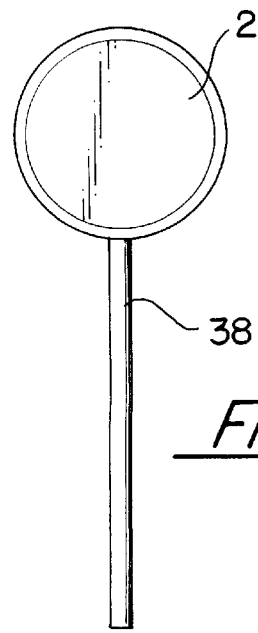
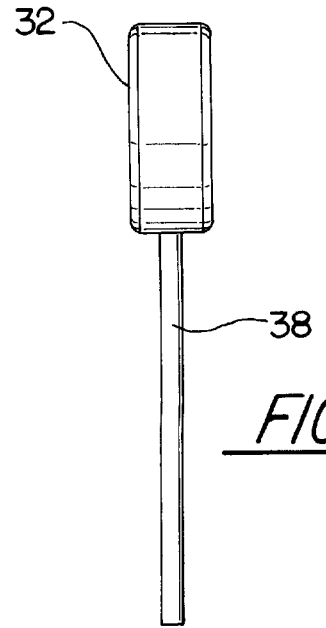
FIG. 11          FIG. 12

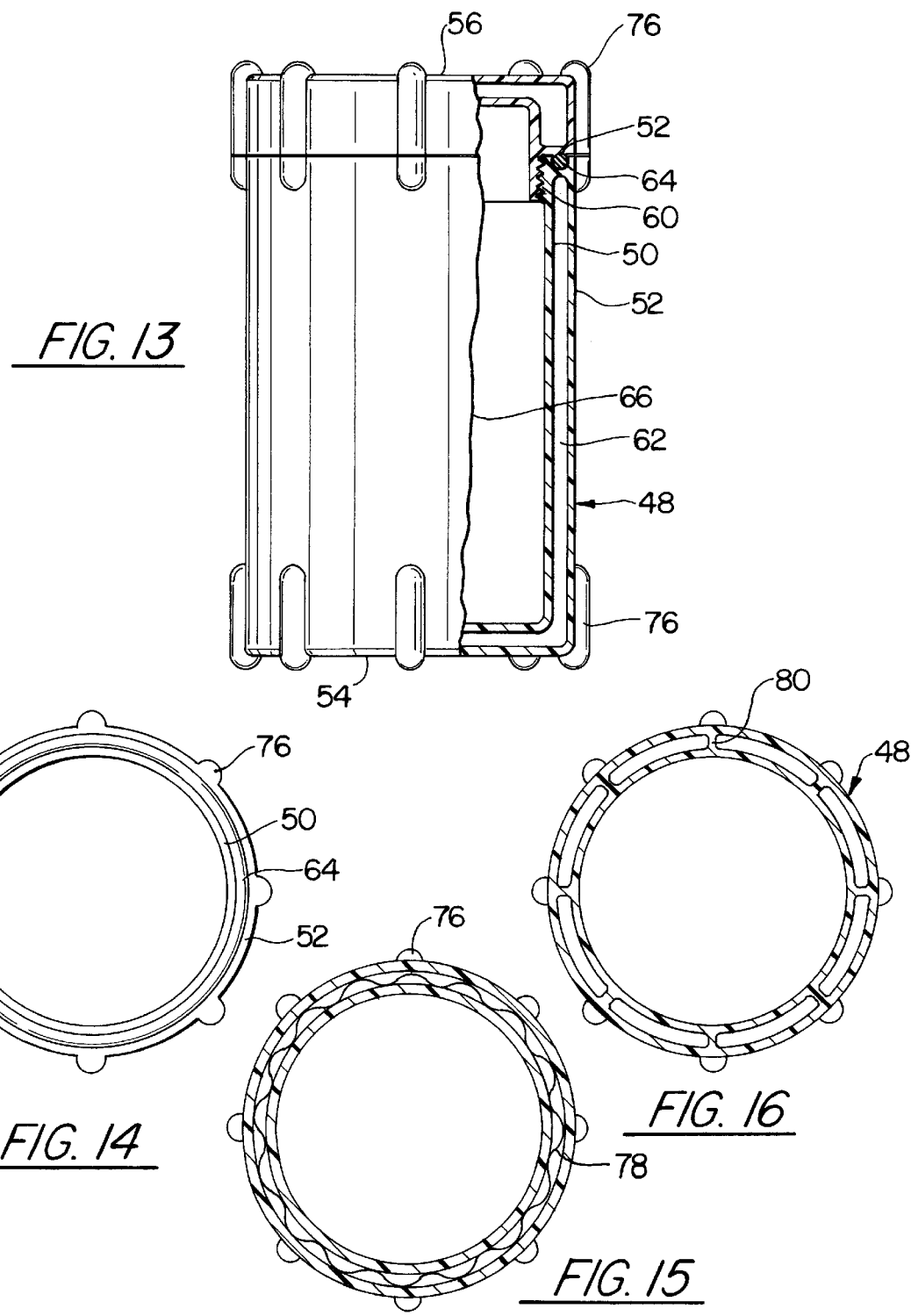

HEALTHFUL DISSOLVABLE ORAL TABLETS, AND MINI-BARS

REFERENCE TO RELATED APPLICATIONS

This application is a continuation-in-part of our application, Ser. No. 08/854,257, filed May 9, 1997, now abandoned.

BACKGROUND OF THE INVENTION

1. Field of the Invention

The field of this invention is healthful tablets and mini-bars which will dissolve in the mouth. The tablets and mini-bars contain active ingredients which maintain or improve health. The tablets may be mounted on lollipop sticks. The ingredients are oxygen supplement, vitamins, minerals, healthful herbs, and dehydrated healthful foods. This invention is also directed to wrappers which fit around a plurality of the tablets stacked end-to-end, around the bars, or around a single tablet on a lollipop stick. Additionally, the field of this invention is thermally insulating containers for everyday use and for emergency canteen containers for disasters. The canteen containers protect their ingredients from temperature changes and are useful for distributing the tablets and mini-bars of this invention, water, dehydrated food, vitamins, supplements, a first aid kit, and necessary supplies in times of disasters.

2. Description of the Related Art

The art is aware of administering active ingredients to people by means of products which will dissolve in the mouth. U.S. Pat. No. 5,286,496 to Stapler et al discloses antibacterial mints wherein the active ingredient is contained in microcapsules and will be released in the oral cavity. U.S. Pat. No. 5,286,748 to Egy describes the topical application to the oral cavity of medicaments to shorten the duration of colds by means of dissolvable tablets. The use of lollipops as carriers for medicaments is also known in the art. Thermally insulating storage containers are known in the art. U.S. Pat. No. 4,444,324 to Grenell shows compartmentalized thermally insulating containers for food, etc.

The oral compositions of the prior art use large quantities of non-therapeutic carriers and minor amounts of active ingredients. One reason for this is that in any one product, only a small amount of active ingredient is needed and the tablets must be of a size which can be handled. The tablets of the prior art are not appealing to children or adults who enjoy a multiplicity of different food tastes such as mother's chicken soup, pizza, fish, turkey and vegetables in that the prior art tablets and mini-bars are made up of a single flavor.

The art is also aware of thermal storage containers for food. U.S. Pat. No. 4,444,324 to Grenell shows compartmentalized thermally insulating containers for food, etc. These compartmentalized containers are made so that each compartment is the same size. These containers would be difficult to find at night if their use as emergency containers was attempted, and these containers would offer no help in signaling for help or in directionally orienting the user. These containers do not have O-rings between the covers and the container to protect against leakage and temperature changes. These containers do not have covers that are attached by a connection. Therefore the covers of the prior art containers can become lost.

SUMMARY OF THE INVENTION

One object of the present invention is to overcome the deficiencies of the prior art tablets, mini-bars, wrappers, and containers. A part of this object is accomplished by providing stable tablets and mini-bars which dissolve in the mouth and are capable of supplying needed healthful agents. Another part of this object is accomplished by providing wrappers for these tablets and mini-bars which provide storage stability and protect against breakage. Another part of this object is accomplished by providing containers for the tablets and mini-bars and other necessary items, which containers are thermally insulated, compartmentalized, sturdy, and provide features which are helpful in times of disaster. It is one object of the present invention to provide the above products while avoiding the inadequacies inherent in the products of the prior art.

The present invention is directed to attractive tablets and mini-bars which contain a multiplicity of healthful ingredients of various types. The tablets and mini-bars are made by extruding distinct segments of active ingredients, binders and attractive colors as endless forms containing these distinct segments, then dividing the completed forms into tablets or mini-bars having the desired size and shape.

A wide variety of active ingredients is useful in the tablets and mini-bars of this invention. Of particular use, are active ingredients which are suitable for daily health conditions and those ingredients which are needed by victims of disaster to keep them alive and functioning until professional help arrives. As examples of active ingredients, oxygen enhancers, vitamins, mineral supplements, nutrients, herbs, mint, soy protein, enzymes, pycnogenols, and dehydrated food supplements may be used. It has recently been established that the administration of vitamins and nutrients such as vitamin E, Co-enzyme $Q_{10}$, vitamin C, alpha lipoic acid, magnesium, fish oils, and flavonoids are of benefit if given around the time of operations or strokes, and that the administration of multiple nutrients is advisable. Thus, one use of the tablets of the present invention is to provide a necessary supply of oxygen enhancers, vitamins, minerals, and agents having an active part in strengthening the immune system in patients prior to surgery while not introducing any large quantities of material into the stomach. Important intended uses of the tablets and mini-bars of this invention are to provide oxygen enhancers, healthful food substances, and vitamins to survivors of natural disasters and to supply these tablets and mini-bars for general use.

A convenient way of carrying the tablets of this invention is in the form of end-to-end stacks. The stacks of tablets and the mini-bars may be surrounded by a thermally insulating shaped wrapper having the same shape as the stack or bar, an inner surface, an outer surface, and a strengthening corrugated body joining the two surfaces. The wrapper is preferably made of thermally insulating aluminum foil. Alternatively, the tablets may be carried on lollipop sticks. To meet the objectives stated above, the tablet stacks and bars are packaged in these thermally insulating wrappers for protection and longer life during storage and delivery into the disaster areas. These packages can be further stored and delivered in emergency thermally insulating containers which are part of the present invention.

Another aspect of the present invention is directed to thermally insulating containers having an inside and an outside wall and can have a single, primary unit or a plurality of secondary containers affixed to the outer cylinder wall of the primary container. All of the containers are double walled to provide protection against changes in temperate and impact on delivery. The thermally insulated containers, which are made of hypo-allergenic material, have multiple purposes, and can serve as canteen containers for the tablets and mini-bars of this invention, water, first aid supplies, vitamins and supplements, dehydrated food, etc. The primary and secondary containers have openings at the top ends. For specialized utility during disaster relief, a container is luminous to provide for ease in locating, it contains a signaling mirror for summoning aid, and has a compass for assistance in getting oriented. At least one of the outer, secondary containers is part of a disaster canteen container. These containers can be removed for easy use and returned to the container and covered. The covers of the canteens are attached so as not to become lost. The present invention provides secondary containers of varying sizes in order to provide thermally insulating containers for everyday use such as single thermally insulating containers for tablets and mini-bars. At least one secondary container serves as a squeezable thermally insulated tube for burn ointments, food products in paste form, sun protective creams, or insect repellents. Another secondary container serves as a firm thermally insulated container for creams and salves.

A primary function of the canteen containers of this invention is to hold oxygen enhancers, water, food supplements, and supplies for disaster survivors until help arrives. Another function is to serve as carriers for these supplies in outer space operations or in other operations where these supplies are not readily available as back-up emergency supplies.

BRIEF DESCRIPTION OF THE DRAWING

FIG. 7 is a horizontal cross-sectional view of a tablet of this invention, showing a coating of dehydrated food.

FIG. 8 is an elevational perspective view, partially in cross-section and partially cut away, showing an extruded cylinder having discrete longitudinal sections of active ingredients, circumferential scoring for easy separation, and a coating of dehydrated food.

FIG. 9 is a top elevational view, partially cut-away, of a mini-bar of the present invention containing discrete sections of active ingredients. A coating of dehydrated food is shown.

FIG. 10 is an elevational end view, partially cut-away, of a mini-bar of the present invention. A coating of dehydrated food is shown.

FIG. 11 is a front view of a tablet of the present invention showing a coating of dehydrated food and mounted on a lollipop stick.

FIG. 12 is a side view of the tablet of the present invention as shown in FIG. 11.

FIG. 13 is an elevational side view, partly in section, of a primary container of one embodiment of the present invention.

FIG. 14 is a horizontal cross-sectional view of the primary or secondary container of the present invention showing the O-ring between the cover and the container wall.

FIG. 15 is a horizontal cross-sectional view of a primary or secondary container of one embodiment of the invention showing strengthening corrugation molded as part of the wall of the inside container.

FIG. 16 is a horizontal cross-sectional view of another embodiment of the primary or secondary container of the present invention showing strengthening units molded between the inside and outside walls.

DESCRIPTION OF THE PREFERRED EMBODIMENTS

Figure 1:
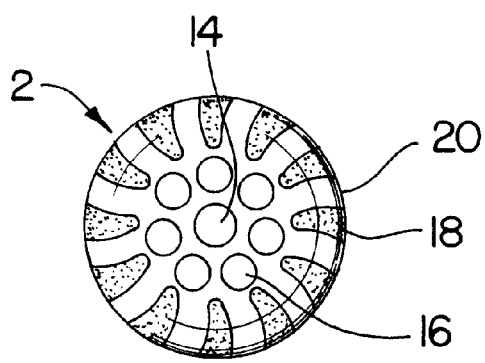
FIG. 1 is a plan view of one embodiment of a tablet according to the present invention.
Figure 2:
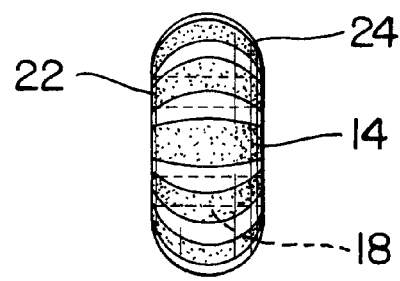
FIG. 2 is an elevational side view of the tablet of FIG. 1.
Figure 3:
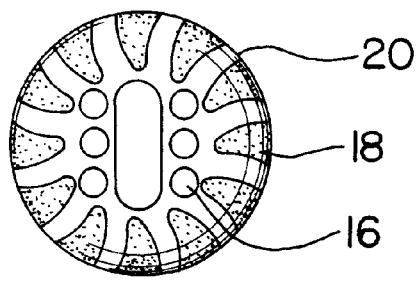
FIG. 3 is a plan view of a second embodiment of a tablet according to the present invention.
Figure 4:
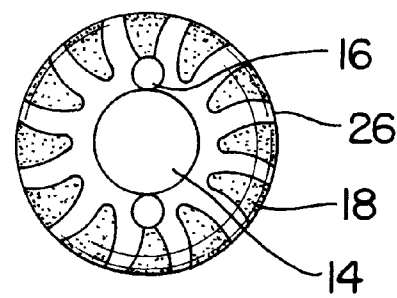
FIG. 4 is a plan view of a third embodiment of a tablet according to the present invention.
Figure 5:
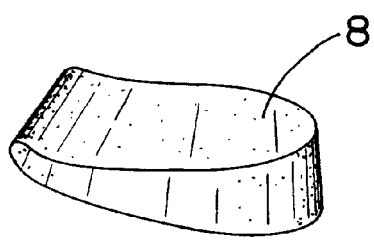
FIG. 5 is an elevational perspective view of a discrete section of a tablet according to the present invention.
Figure 6:
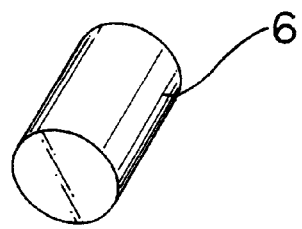
FIG. 6 is an elevational perspective view of a second discrete section of a tablet according to the present invention.
Figure 17:
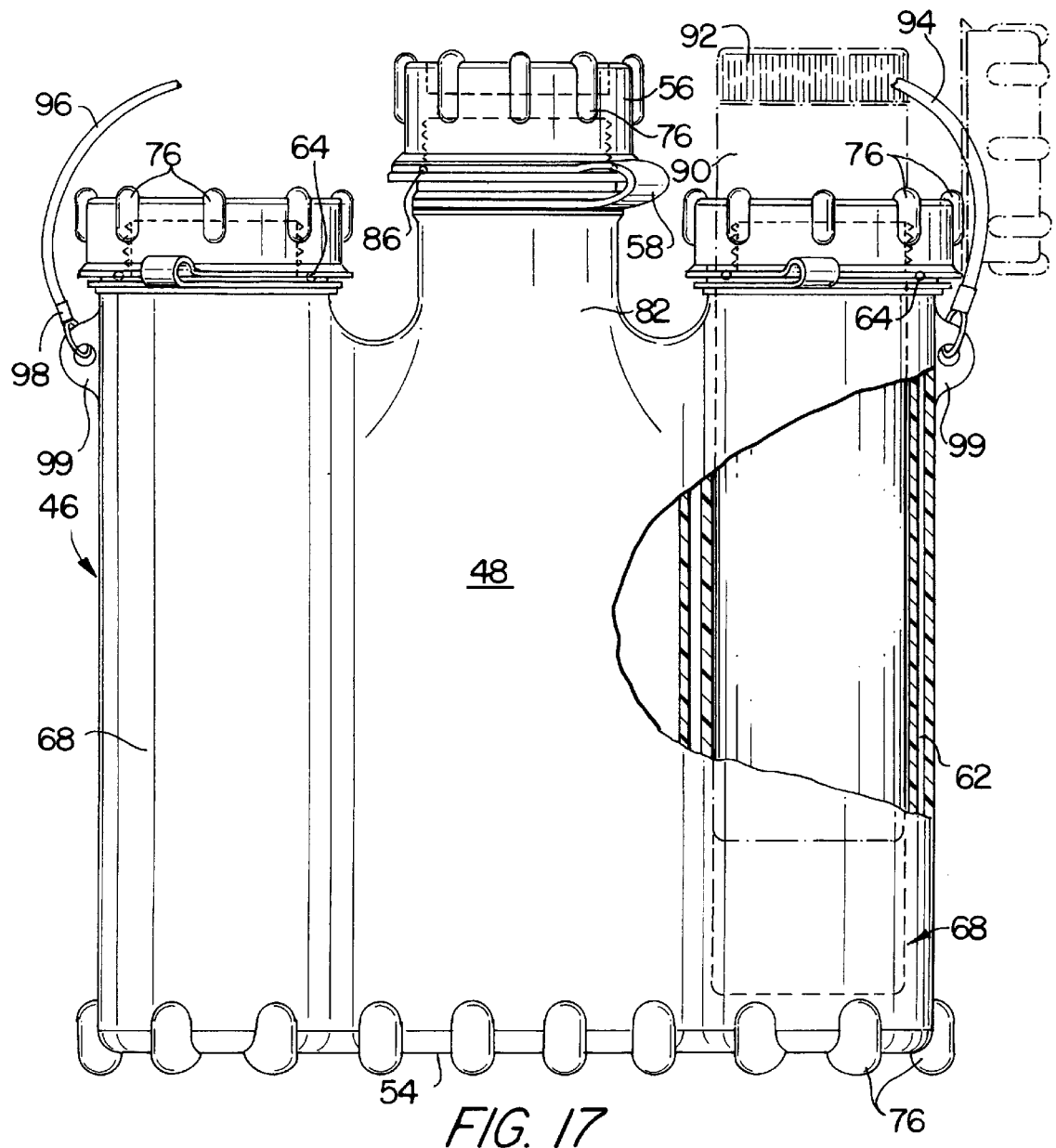
FIG. 17 is an elevational side view, partially in section, of the primary canteen container showing the O-ring between the container and the container wall and showing the attachment of the covers to the container and the lanyard holders.
Figure 18:
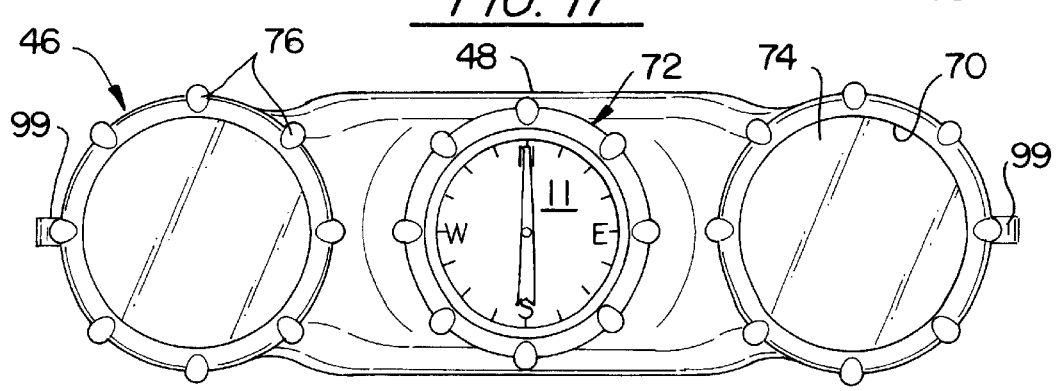
FIG. 18 is a top plan view of the primary canteen container showing a compass in the cover attachment and the lanyard holders.
Figure 19:
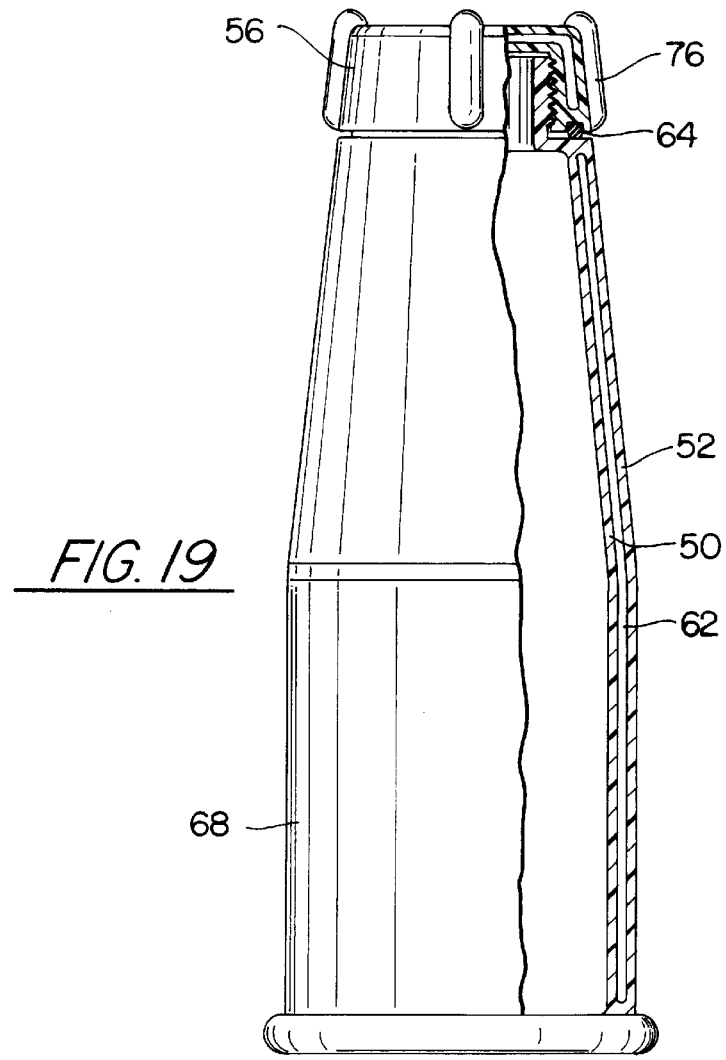
FIG. 19 is an elevational side view, partially in section, showing a thermally insulating squeezable container of this invention.
Figure 20:
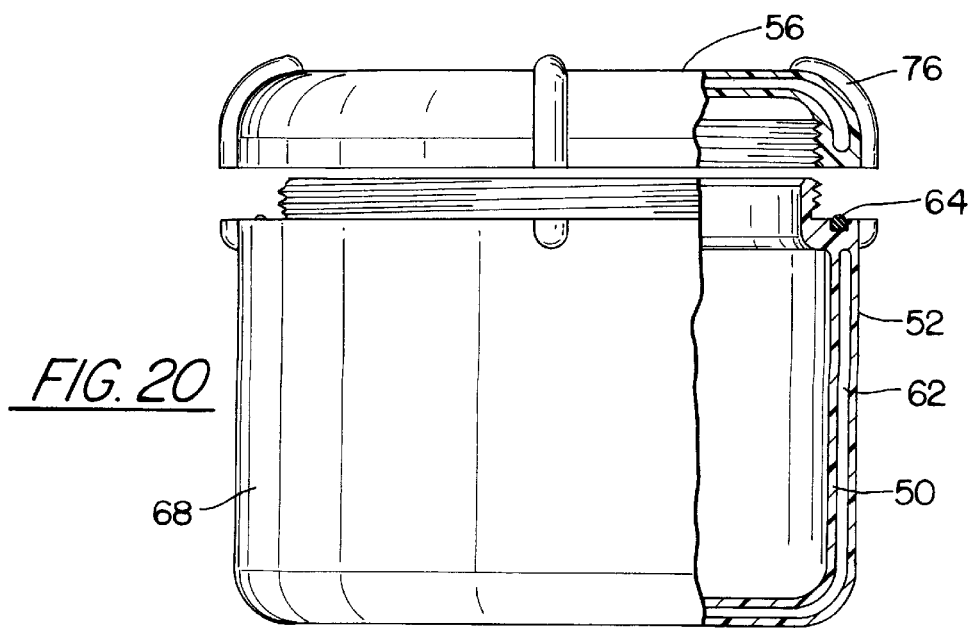
FIG. 20 is a side elevational view, partly in section, showing a thermally insulating cream container of this invention.
Figure 21:
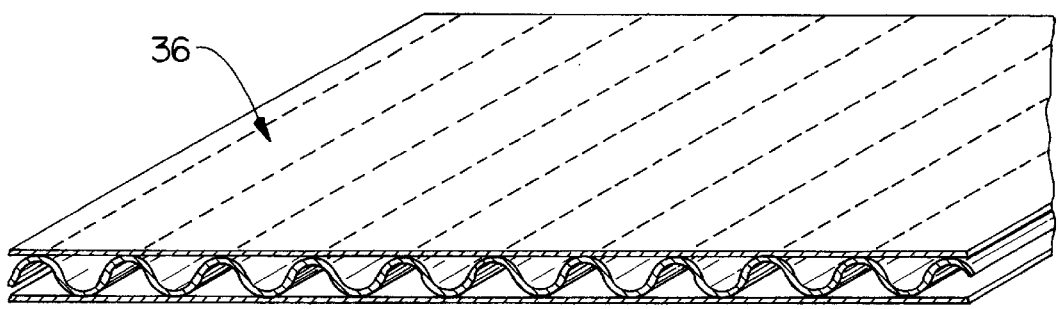
FIG. 21 is an elevational perspective view of a thermally insulating wrapping sheet of aluminum foil having a first piece of material, a second piece of material, and a corrugated piece between the first and second pieces, which sheet has been prepared by extrusion molding.
Figure 23:
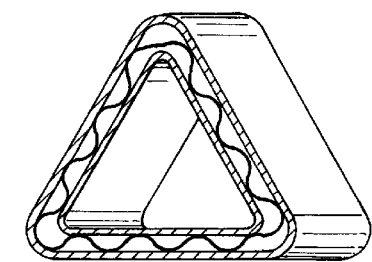
FIG. 23 is a cross-sectional elevational perspective view of a thermally insulating protective wrapper in the shape of a triangle for tablets according to the present invention, which wrapper has been prepared by extrusion molding.
Figure 25:
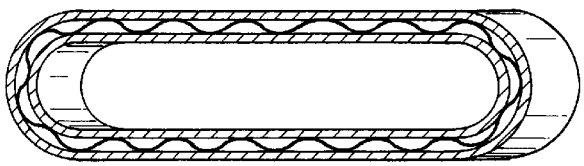
FIG. 25 is a cross-sectional elevational perspective view of a thermally insulating protective wrapper in the shape of an oval for tablets and mini-bars of the present invention, which wrapper has been prepared by extrusion molding.
Figure 24:
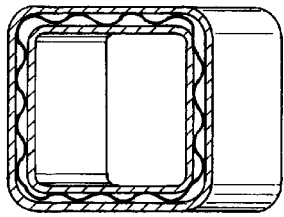
FIG. 24 is a cross-sectional elevational perspective view of a thermally insulating protective wrapper in the shape of a square for tablets according to this invention, which wrapper has been prepared by extrusion molding.
Figure 22:
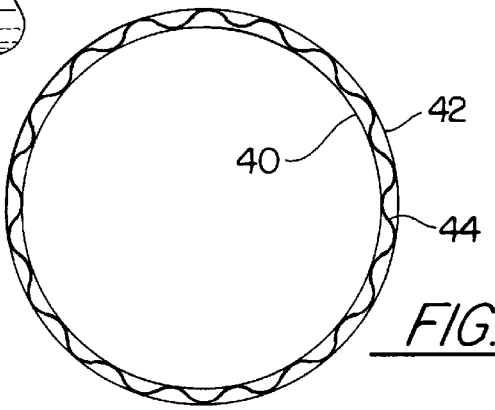
FIG. 22 is a cross-sectional view of a thermally insulating protective wrapper in the shape of a circle for tablets according to the present invention, which wrapper has been prepared by extrusion molding.
Figure 26:
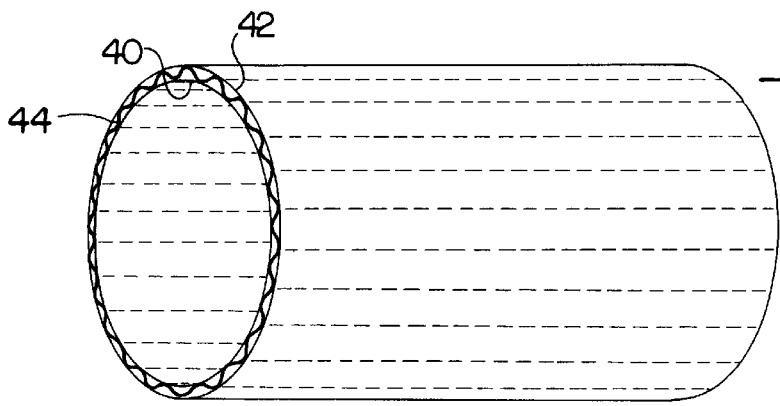
FIG. 26 is an elevational perspective view of a thermally insulating protective wrapper in the shape of a circle for tablets of this invention, which wrapper has been prepared by extrusion molding.

The present invention will now be described with reference to the above drawing, like numerals referring to like parts throughout the description.

Referring to FIGS. 1–12, the tablets and mini-bars of this invention will be described.

A tablet 2 or mini-bar 4 of the present invention may be prepared by insert plug molding. In this method, a plurality of circular 6 or irregularly shaped 8 discrete segments are individually prepared and plugged together following preparation.

The preferred method of preparation is extrusion molding. In this method, a central core 14 and a plurality of surrounding circular 16 and irregularly shaped 18 bodies of active ingredients having desired configurations are extruded from an extrusion molding apparatus. Each discrete body 16 18 may contain an active ingredient, a binder, and sufficient moisture to allow extrusion. When desired, an active ingredient may be incorporated into time-release capsules (not shown) prior to extrusion. Simultaneously, another combination of active ingredient, binder, and moisture, is extruded in such a manner that the spaces between the discrete segments 16 18 are filled in and a cylindrical body having discrete segments 16 18 of active ingredients surrounded by a matrix 20 containing an active ingredient is formed. The resulting cylindrical body may be divided into tablets 2 having first end surfaces 22, second end surfaces 24, and a circumferential edge 26 joining the first 22 and second 24 end surfaces. The tablet 2 or mini-bar 4 may be covered 32 with a mixture of healthful dehydrated food, such as mother's chicken soup, pizza, turkey, fish or vegetables.

The tablets 2 and mini-bars 4 of the present invention, unlike tablets and lozenges of the prior art, do not employ dicalcium phosphate as a filler. This compound leads to decreased absorption of vitamins and minerals. When absorbed into the bloodstream, dicalcium phosphate collects in the arteries to cause arteriosclerotic heart disease, in the joints to cause arthritis, and in the soft tissue to cause excessive skin wrinkles.

A wide variety of active ingredients may be incorporated into the tablets 2 and mini-bars 4 of the invention. The particular combination of ingredients selected will depend upon the anticipated end use of the tablets 2 and mini-bars 4.

A discussion of the preferred ingredients follows.

Chlorella is the closest thing to a perfect natural food and is the best nutritional cleanser. It contains potent acid antioxidants to counter free radicals.

Antioxidants, such as RRR-tocopherol, described in U.S. Pat. No. 4,695,590, have a number of beneficial properties, including the slowing down of the aging process, and are included in the tablets 2 and mini-bars 4 of this invention. Other antioxidants, such as Vitamin C, Vitamin E, beta-carotene, plant flavonoids, and selenium also have recognized beneficial properties and are included in the tablets 2 and mini-bars 4 of the present invention.

St. John's wort is a positive mood enhancer.

Enzymes, such as pancreatin, papain, bromelain, trypsin, lipase, amylase, chymotrypsin, papaya, and rutin are necessary agents for the vital function of bodily activities. Bromelain, which is found in the stems of pineapples, can also help relieve aching, inflammation, and swelling in joints.

The cooking of foods to 140° F. destroys all active enzymes. Therefore, a source of active compounds is needed for continued health. Co-enzymes are the heat stable portions of enzymes which combine with inactive enzymes to render them capable of effecting their proper action. Co-enzyme $Q_{10}$ is one of the most important daily supplements. This co-enzyme helps maintain healthy hearts, circulatory systems, and immune systems. The incorporation of enzymes and co-enzymes into timed-release capsules which will not dissolve in the mouth or stomach, but will dissolve in the bowel ensures proper delivery of these vital agents.

Minerals, such as zinc, the above-mentioned selenium, magnesium, manganese, iron, copper, and molybdenum are known to be necessary enzyme activators. Many diets contain insufficient quantities of these minerals. One purpose of the tablets 2 and mini-bars 4 of the present invention is to supply sufficient quantities of these necessary minerals when the tablets 2 or mini-bars 4 are taken on a daily basis. In preferred embodiments, the minerals are present in chelated form or are of a colloidal size for easy and complete absorption.

Vitamins, necessary chemicals to prevent deficiency diseases, are natural ingredients in the tablets 2 and mini-bars 4 of the present invention to protect not only disaster survivors, but also those of the population whose diets lack these essential materials. Vitamin A, the B-complex vitamins, Vitamins C, D, E, and U, and biotin are suitable for use in the tablets 2 and mini-bars 4 of this invention. Folic acid, another essential vitamin, participates in the manufacture of new cells and participates in the formation of erythrocytes.

Stabilized oxygen supplements and enhancers prove especially useful in natural disasters wherein the air is depleted of its normal supply of oxygen. Oxygen supplements and enhancers are also beneficial for everyday use and is especially useful for seniors. Stabilized oxygen supplement in the form of Aquagen® or OXYflex® is helpful in supplying needed quantities of oxygen to the system. Such supplements comprise sodium chloride, sodium carbonate, trace minerals, distilled water, and neutralized rice. The natural compound, dimethyl glycine, is known for its ability to enhance oxygen utilization. The herb *Ligusticum wallichii* is known to increase the speed of blood flow and elevate cerebral blood circulation, thus increasing oxygen uptake especially in the brain. Another herb, Radix Salviae Miltiorrhizae, enhances blood circulation and regulates blood pressure. Rutin, a flavonoid found in plants, enhances the oxygen-carrying ability of the blood. For the sake of simplicity, compounds such as those named above which supply oxygen, enhance oxygen uptake, or increase blood flow to cells, are termed oxygen enhancers in this disclosure.

Soy protein is a known additive which causes lowered blood cholesterol and a corresponding lowered LDL. This agent is a useful component of the tablets and bars of this invention.

Natural products are being rediscovered as sources of energy. Accordingly, echinacea, cactus, yucca (a plant native to the American West and Southwest), golden seal, spirulina, royal jelly, bee pollen, wheatgrass, kelp, dulse, Irish moss, grape seed extract, cranberry extract, kava kava, ginseng, nettles, corn, alfalfa, fo-ti, pau-d'arco, fennel seed, schizandra, barley grass, oat bran, acacia gum, saussurea, cat's claw, ginger, licorice root, coyette, ginkgo biloba, bilberry, cayenne, aloe vera, garlic, saw palmetto, burdock root, hawthorn berry, gotu kola, juniper berries, pumpkin seeds, prickly ash bark, white willow bark, and slippery elm bark are considered valuable ingredients in the tablets 2 and mini-bars 4 of this invention. Each of these natural products is known in the art, and the preparation of these products is known to those skilled in the art. The above-mentioned garlic possesses healing properties, strengthens the immune system, lowers the blood cholesterol level, and cleanses the blood. Cranberry extract helps promote a healthy urinary system. Licorice root, one of the most commonly used herbal remedies in the world, is considered to soothe and safeguard the body.

Amino acids, such as L-carnitine, L-arginine, L-glutamine, N-acetylcysteine, L-glutathione, L-tyrosine, DL-phenylalanine, L-lysine, L-taurine, and L-arginine/L-ornithine make up proteins which are essential for the carrying out of bodily processes. These compounds form ingredients in the tablets 2 and mini-bars 4 of this invention.

Mint is any of the various plants of the mint family whose leaves are used for flavoring and coloring. Plants suitable for use in the tablets of the invention are spearmint, basil, peppermint, and bergamot. These ingredients provide a variety of flavor and color to the tablets 2 and mini-bars 4.

In order to provide added nutrition and flavor appeal, the tablets 2 and mini-bars 4 may contain dehydrated foods, such as vegetables, turkey, fish, pizza and chicken soup, especially mother's chicken soup. Preferably, the dehydrated food is used as a covering for the tablet 2 or mini-bar 4.

In the preferred embodiment, tablets 2 and mini-bars 4 of the present invention are prepared by extrusion of a solid cylinder containing discrete segments 16 18 surrounded by a matrix 20. Each discrete segment 16 18 and the matrix 20 contains an active ingredient described above. More than a single active ingredient is permissible if no adverse interactions occur. In addition to the active ingredient, each segment 16 18 and the matrix 20 contains sufficient water to enable the ingredient to be extrudable and sufficient binder to maintain integrity.

Following extrusion, the cylinders are sliced into individual tablets 2, grouped together in end-to-end abutment into a convenient number of separate tablets 2, and wrapped. The cylinders may be sliced into segments 34 which will result in a convenient number of tablets 2. The individual tablets 2 or segments 34 may then be coated 32 with dehydrated food and wrapped 36. Following extrusion, the mini-bars 4 of this invention are coated 32 with dehydrated food and wrapped 36 for transport.

The tablets 2 and mini-bars 4 of the present invention find utility in providing nutrition and pleasant taste to people under normal circumstances, people who are deprived of food while awaiting surgery, and survivors of natural disasters.

The specific ingredients incorporated into the tablets 2 and mini-bars 4 of this invention and the amounts of these ingredients are dependent upon the intended purpose. The following specific Examples illustrate a number of tablets designed for particular purposes.

EXAMPLE I

| Tablets or mini-bars for combating colds | |
|---|---|
| Dehydrated mother's chicken soup | 2 oz. |
| Oxygen supplement | 200 mg. |
| Cayenne | 50 mg. |
| Soy protein | 100 mg. |
| Bee pollen | 100 mg. |
| Ginseng | 100 mg. |
| Zinc | 50 mg. |
| Golden seal | 100 mg. |
| Vitamin C | 100 mg. |
| Vitamin E | 100 mg. |
| Echinacea | 200 mg. |

EXAMPLE II

| Tablets or mini-bars for aiding memory | |
|---|---|
| Dehydrated food | 2 oz. |
| Ginkgo biloba | 100 mg. |
| Gotu kola | 150 mg. |
| Bee pollen | 100 mg. |
| Soy protein | 150 mg. |
| Oxygen supplement | 300 mg. |
| Ginger root | 75 mg. |
| Yucca root | 200 mg. |
| Vitamin B-12 | 100 mg. |
| Vitamin C | 150 mg. |
| Vitamin E | 100 mg. |
| Phosphatidyl serine complex | 50 mg. |
| Shark cartilage | 200 mg. |
| Cayenne | 100 mg. |
| Folic acid | 150 mg. |
| Ginseng root | 200 mg. |
| Chlorella | 100 mg. |

EXAMPLE III

| Tablet or mini-bar for combating fatigue | |
|---|---|
| Dehydrated food | 2 oz. |
| Shark cartilage | 200 mg. |
| Co-enzyme $Q_{10}$ | 50 mg. |
| Kava kava | 150 mg. |
| Yucca root | 200 mg. |
| Papaya enzyme | 100 mg. |
| Folic acid | 50 mg. |
| Grape seed extract | 30 mg. |
| Ginger root | 75 mg. |
| Oxygen supplement | 300 mg. |
| Soy protein | 150 mg. |
| Vitamin C | 150 mg. |
| Vitamin E | 100 mg. |
| Ginseng root | 200 mg. |
| Bee pollen | 150 mg. |
| Octacosanol | 200 mg. |
| Royal jelly | 150 mg. |
| Chlorella | 100 mg. |

EXAMPLE IV

| Tablet or mini-bar for improving the heart | |
|---|---|
| Dehydrated food | 2 oz. |
| Oxygen supplement | 300 mg. |
| Soy protein | 150 mg. |
| Folic acid | 50 mg. |
| Potassium | 20 mg. |
| Selenium | 40 mg. |
| Calcium | 100 mg. |
| Vitamin B-12 | 100 mg. |
| Hawthorn berry | 100 mg. |
| Ginger root | 75 mg. |
| Vitamin C | 150 mg. |
| Vitamin E | 100 mg. |
| Vitamin B-3 | 60 mg. |
| Co-enzyme $Q_{10}$ | 30 mg. |
| L-taurine | 100 mg. |
| Shitake mushroom extract | 100 mg. |
| Omega-3-fish oil | 200 mg. |
| Ginseng root | 200 mg. |
| Chlorella | 100 mg. |

EXAMPLE V

| Survival tablets or mini-bars | |
| --- | --- |
| Dehydrated food | 2 oz. |
| Oxygen supplement | 400 mg. |
| Co-enzyme $Q_{10}$ | 50 mg. |
| Yucca root | 100 mg. |
| Garlic and parsley | 300 mg. |
| Folic acid | 50 mg. |
| St. John's wort | 200 mg. |
| Vitamin C | 150 mg. |
| Vitamin E | 100 mg. |
| Papaya enzyme | 100 mg. |
| Soy protein | 150 mg. |
| Ginkgo biloba | 100 mg. |
| Royal jelly | 100 mg. |
| Licorice root | 150 mg. |
| Gotu kula | 100 mg. |
| Cayenne | 100 mg. |
| Pycnogenol | 200 mg. |
| Wild yam root | 100 mg. |
| Bromelain | 100 mg. |
| Ginseng root | 200 mg. |
| Chlorella | 100 mg. |

EXAMPLE VI

| Tablet or mini-bar for aiding circulation | |
| --- | --- |
| Dehydrated food | 2 oz. |
| Oxygen supplement | 300 mg. |
| Yucca root | 200 mg. |
| Ginseng root | 100 mg. |
| Ginkgo bilboa | 100 mg. |
| Shitake mushroom extract | 200 mg. |
| folic acid | 50 mg. |
| Oat bran | 75 mg. |
| Licorice root | 100 mg. |
| Ginger root | 75 mg. |
| Cayenne | 100 mg. |
| Vitamin B-12 | 100 mg. |
| Vitamin C | 150 mg. |
| Vitamin E | 100 mg. |
| L-Lysine | 50 mg. |
| L-Proline | 50 mg. |
| Hawthorn berry | 100 mg. |
| Bromelain | 100 mg. |
| Omega-3-fish oil | 150 mg. |
| Garlic and parsley | 150 mg. |
| Co-enzyme $Q_{10}$ | 50 mg. |
| Chlorella | 100 mg. |

EXAMPLE VII

| Tablet or mini-bar for treating prostate problems | |
| --- | --- |
| Dehydrated food | 2 oz. |
| Oxygen supplement | 200 mg. |
| Saw palmetto | 300 mg. |
| Pygeum bank | 50 mg. |
| Golden seal | 500 mg. |
| Cranberry extract | 200 mg. |
| Yucca root | 200 mg. |
| Vitamin C | 150 mg. |
| Vitamin E | 100 mg. |
| Chlorella | 100 mg. |
| Aloe vera | 150 mg. |
| Co-enzyme $Q_{10}$ | 50 mg. |
| Zinc | 50 mg. |
| Garlic and parsley | 150 mg. |

-continued

| Tablet or mini-bar for treating prostate problems | |
| --- | --- |
| Pumpkin seed oil | 200 mg. |
| Ginseng root | 600 mg. |

EXAMPLE VIII

| Pre-surgical tablet | |
| --- | --- |
| Vitamin C | 150 mg. |
| Vitamin E | 100 mg. |
| Soy protein | 150 mg. |
| Oxygen supplement | 200 mg. |
| Papaya enzyme | 100 mg. |
| Wild yam root | 100 mg. |
| Ginger | 100 mg. |
| Ginkgo biloba | 40 mg. |
| Grape seed extract | 30 mg. |
| Gotu kola | 150 mg. |
| Ginseng root | 150 mg. |
| Hawthorn berry | 100 mg. |

EXAMPLE IX

| Tablets or mini-bars for traveling | |
| --- | --- |
| Dehydrated mother's chicken soup | 2 oz. |
| Oxygen supplement | 200 mg. |
| Papaya enzyme | 100 mg. |
| Zinc | 50 mg. |
| Bee pollen | 100 mg. |
| Ginkgo biloba | 40 mg. |
| Gotu kola | 40 mg. |
| Soy protein | 100 mg. |
| Wild yam root | 100 mg. |
| Kava kava | 150 mg. |
| Valerian | 150 mg. |
| Green phyto | 200 mg. |
| Vitamin C | 100 mg. |
| Vitamin E | 100 mg. |
| Garlic and parsley | 150 mg. |
| Ginseng root | 200 mg. |
| Chlorella | 100 mg. |

EXAMPLE X

| Tablet or mini-Bar for playing active sports | |
| --- | --- |
| Dehydrated food | 2 oz. |
| Oxygen supplement | 300 mg. |
| Yucca root | 100 mg. |
| Soy protein | 100 mg. |
| Ginkgo biloba | 50 mg. |
| Gotu kola | 100 mg. |
| Papaya enzyme | 100 mg. |
| Cayenne | 100 mg. |
| Licorice root | 100 mg. |
| Ginseng root | 200 mg. |
| Hawthorn berry | 100 mg. |
| Garlic and parsley | 100 mg. |
| Chromium dicholinate | 150 mg. |
| Vitamin C | 150 mg. |
| Vitamin E | 100 mg. |
| Co-enzyme $Q_{10}$ | 50 mg. |
| Chlorella | 100 mg. |

EXAMPLE XI

| tablet or mini-bar for arthritis | |
|---|---|
| Dehydrated food | 2 oz. |
| Glucosamine | 250 mg. |
| Chondroitin | 200 mg. |
| Calcium | 300 mg. |
| Vitamin D | 100 mg. |
| Omega-3-fish oil | 100 mg. |
| Shark cartilage | 300 mg. |
| Oxygen supplement | 200 mg. |
| Vitamin B-5 | 200 mg. |
| Yucca root | 200 mg. |
| Vitamin C | 150 mg. |
| Vitamin E | 100 mg. |
| Cranberry extract | 150 mg. |
| Aloe vera | 150 mg. |
| Cayenne | 100 mg. |
| Bromelain | 200 mg. |
| Willow bark | 100 mg. |
| Co-enzyme $Q_{10}$ | 50 mg. |
| Ginseng root | 200 mg. |
| Chlorella | 100 mg. |

In the above Examples, when oxygen supplement is named, Aquagen® was used. Where the Examples mention dehydrated food, generically, mother's chicken soup was used and the dehydrated food was used as a coating 32. Where the Examples refer to garlic and parsley, these ingredients were used in equal amounts.

Referring to FIGS. 21–26, the wrapping 36 of the tablets 2, mini-bars 4, segments 34 and lollipops 38 will now be described.

Either the groups of separate tablets 2 or mini-bars 4, the segments 34, or the lollipops 38 are then wrapped. The thermal insulating protective wrapper 36 of the preferred embodiment of the invention comprises an inner shaped piece 40, an outer shaped piece 42, and a corrugated piece 44 between the inner 40 and outer 42 shaped pieces. The wrappers 36 are manufactured by known methods of extrusion molding. The wrappers 36 may be extruded as a single sheet which will later be wrapped around the tablets, 2 tablet stacks, segments 34, mini-bars 4, or lollipops 38 of this invention. Alternatively, the wrappers 36 may be extruded in shaped form to be filled by the tablets 2, stacks, segments 34, or mini-bars 4 of the present invention. Shapes may include circular, triangular, oval, or square. Ends of the protective wrapper 36 extend beyond the shaped segment 24 of tablets 2 and are folded over for airtight sealing. This protective wrapper 36 offers prolonged storage stability, protection against temperature change, and protection against jarring during shipment and delivery. The preferred material for the wrapper 36 is aluminum foil, although a flexible plastic may be used. The preferred wrapper 36 material of the invention is made of hypoallergenic material.

In another embodiment of this invention, the tablet 2 is mounted on a lollipop stick 38. To prepare this embodiment, a hole slightly larger than the diameter of the stick 38 is placed in the tablet 2, preferably by drilling, and the end of the stick 38, preferably wetted with a non-toxic adhesive, is inserted into the hole. In this embodiment, the tablets 2 are individually wrapped with the thermal insulating protective wrapper 36. Preferably, this is accomplished by crimping ends of two separate protective sheets together. A notch is placed at the top of the protective wrapper 36 to allow for easy opening.

Once the tablets 2 and mini-bars 4 are wrapped, they may be packaged in an emergency thermally insulating canteen container 46 for delivery to survivors of disasters. The preferred emergency canteen containers 46 are constructed of rugged plastic by the blow molding process.

The canteen containers 46 will be described with reference to FIGS. 13–20.

A preferred canteen container 46 according to the present invention contains a primary container 48 having inner 50 and outer 52 cylindrical walls, a bottom 54, and a removable screw cover 56 which is attached by a connecting strap 58 to a threaded opening 60 to prevent loss. The space 62 between the inner 50 and outer 52 walls forms a thermally insulating space 62. The primary container 48 has a cylindrical inner shape. The primary container 48 has an O-ring 64 between the container body 66 and the cover 56. The container 48 further contains a plurality of secondary containers 68 affixed to the outer cylindrical wall 52 of the primary container 48, which secondary containers 68 have removable screw-top covers 56 attached to the body portions 66 of the containers 68, thermal insulating spaces 62, and O-rings 64 to ensure a tight seal.

It is preferred that the top central cover 56 is circular in shape and has an indentation 70 which contains a compass 72 in order to help disaster survivors regain their orientation. Also, it is preferred that the secondary container 68 or the primary container 48 has a metal signaling mirror 74 attached to a cover 56 thereof. Such mirror 74 should be made of stainless steel rather than glass to avoid breakage.

Since relief efforts are carried out during the night as well as during the day, it is preferred that the canteen containers 46 of the present invention be coated with luminous paint so as to be visible to disaster survivors. Optionally, the containers 46 may be manufactured from plastic which has luminous materials incorporated therein.

The containers 46 contains sturdy bumpers 76 on both the top 56 and bottom 54 so as to protect the containers 46 during delivery. The bumpers 76 also serve as a grip for helping in opening and closing the covers 56.

In order to form a tight seal for protection of the contents during storage and delivery, there is an O-ring 64 placed at the top of the inner 50 and outer 52 wall, which O-ring 64 is compressed by the screw cover 56 when the primary container 48 or a secondary container 68 is closed. It is preferred that both the primary container 48 and all of the secondary containers 68 be equipped with an O-ring 64 for assurance of a tight seal.

In addition to containing a thermally insulating space 62 which aids in protecting the contents of the primary 48 and secondary 68 containers against changes in temperature, the space 62 between the inner 50 and outer 52 wall of these containers 48 68 may contain a corrugated sheet 78 incorporated in the blow molding process which adds strength to prevent damage on delivery. As an alternative to a corrugated sheet 78, strength may be provided by a plurality of connecting pieces 80 which connect the inner walls 50 and the outer walls 52 of these containers 48 68.

There is a plurality, preferably two, of secondary containers 68 around the periphery of the primary container 48. Each of these secondary containers 68 is made from the same high-impact plastic material as the primary container 48 by blow molding the complete container 46 as a single piece. Each of these secondary containers 68 has a top screw-on cover 56 which is connected to a neck 82 by a connecting strap 58 to avoid loss of the cover 56. Also, each secondary container 68 has a wall 52 which is contiguous with the outer wall 52 of the primary container 48.

In a most preferred embodiment of the secondary container 68, there is an outer wall 52, a thermal insulating space 62, and an inner wall 50. The outer wall 52 is fixedly attached to a screw neck 82 containing a screw-on cover 56. The screw neck 82 has a diameter essentially the same as the diameter of the outer wall 52. The neck 82 and cover 56 are connected by a connecting strap 58 which contains a circular ring 86 at each end which is slidable about the neck 82 and cover 56. The inner wall 50 of the secondary container 68 is not affixed to the outer wall 52 and constitutes an insertable container 90 which may be removed from the outer wall 52 of the secondary container 68. The insertable container 90 has a screw-on top 92 which may be easily connected to the distal end 94 of a lanyard 96. A clip-on attachment (not shown) is preferred. The proximal end 98 of the lanyard 96 is fixedly attached to the outer wall 52 of the secondary container 68 by a connecting ring 99. Thus, when the insertable container 90 is removed from the secondary container 68, the lanyard 96 may be secured to the top 92 of the insertable container 90, and the top 92 may be removed without fear of loss.

It is preferred that one of the secondary containers 68 have squeezable sides and thus be capable of holding liquids which may dispensed without waste in a zero-gravity environment or may dispense food or topical applications having a creamy consistency. One such ingredient is preferably sunscreen.

Another preferred secondary container 68 is an insulated container having a screw top and adapted to hold a topical application of cream consistency, such as sunscreen.

A plurality of essentials for survival may be delivered to survivors of natural disasters with the above container 46. The central primary canteen container 48 is filled with water. One of the secondary containers 68 is filled with the healthful tablets 2 or mini-bars of this invention. Another secondary container 68 contains a first aid kit. Other secondary containers 68, if present, are reserved for supplies peculiar to the type of disaster encountered or may contain additional water. Examples of additional supplies are flashlights, miniature radios, and chemical hand warmers.

Figure 27:
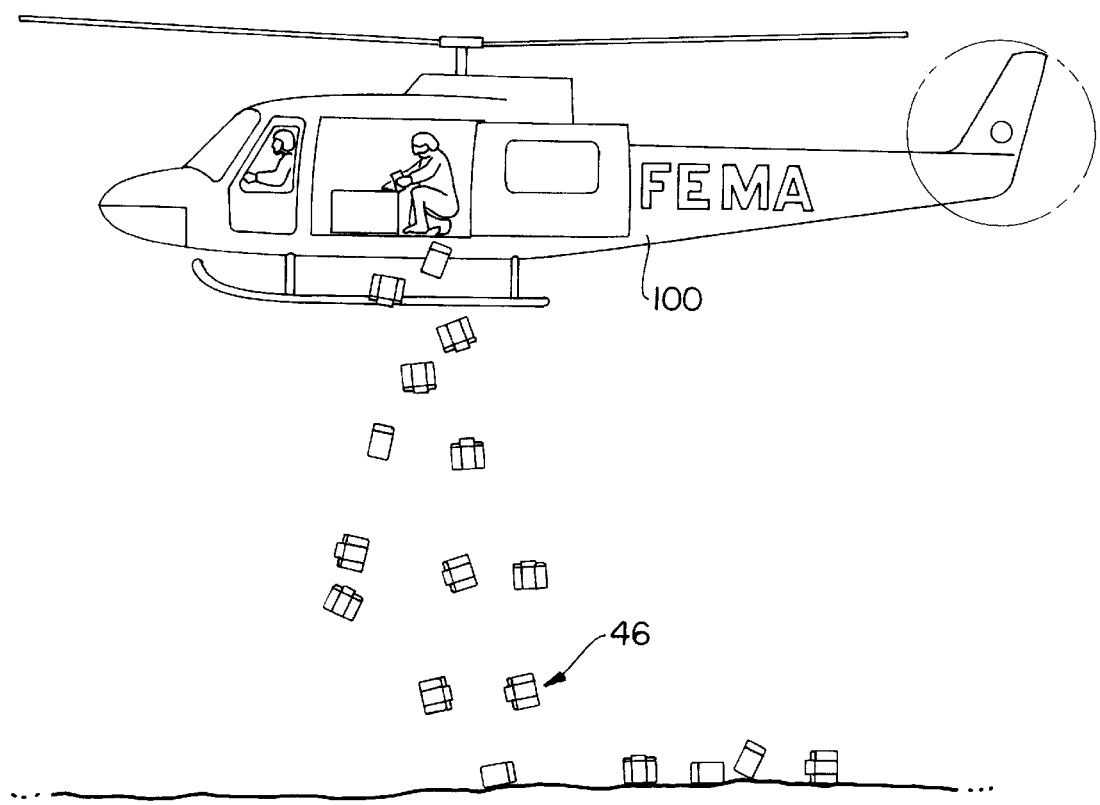
FIG. 27 shows a FEMA helicopter dropping emergency canteen containers of the present invention into disaster areas on land or water.
Figure 28:
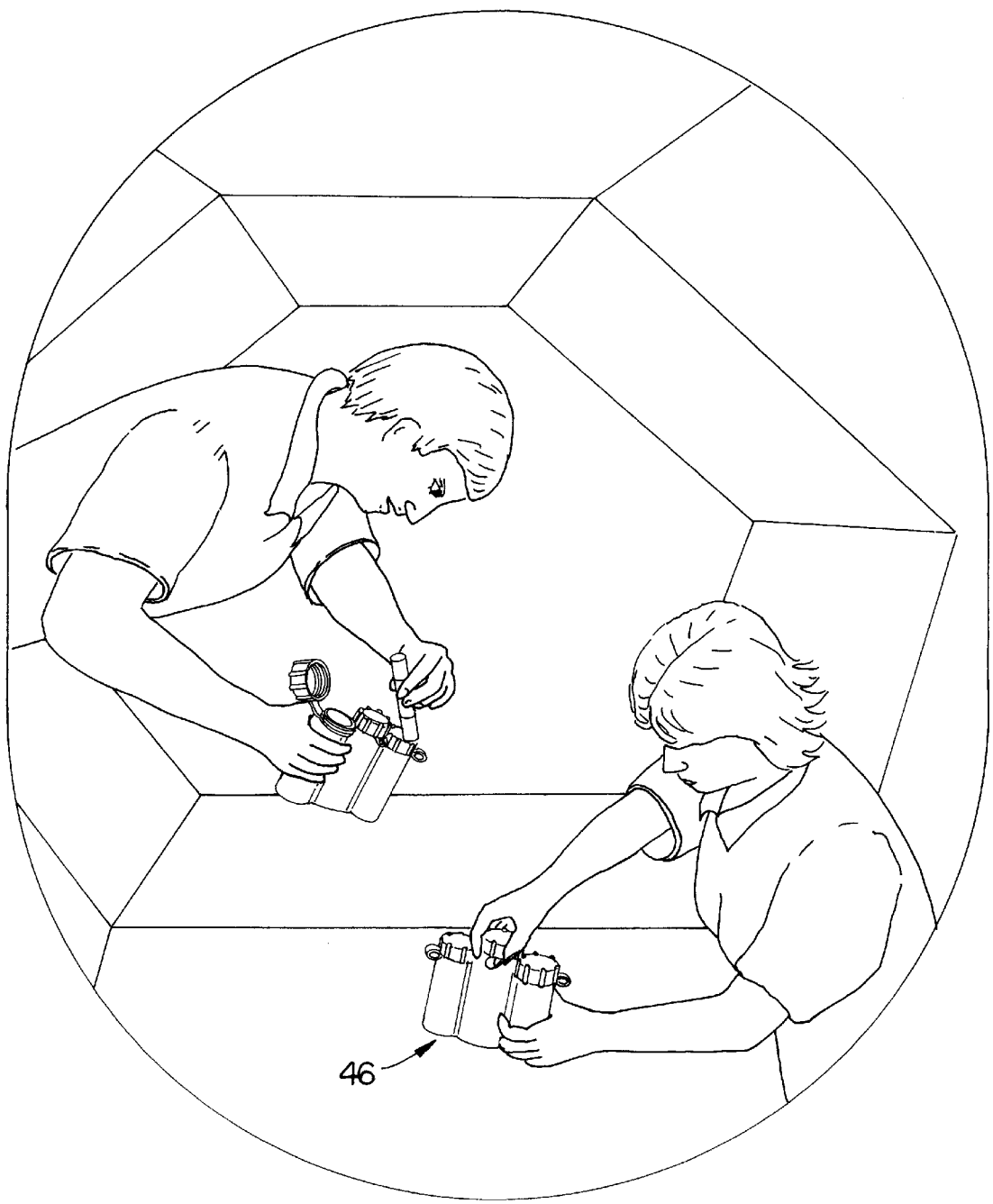
FIG. 28 shows astronauts using the canteen containers of the present invention as an emergency back-up system.

Particular contemplated uses of the tablets, mini-bars, and containers of this invention will now be discussed with reference to FIGS. 27 and 28.

It is contemplated that these filled disaster survival canteen containers 46 will be stored in FEMA distribution sites and taken by truck or helicopter 100 to areas where they are needed. If distributed by helicopter 100, the fact that the containers 46 will float and are luminous is an advantage leading to the possibility of being successfully delivered.

An additional use of the canteen containers 46 filled with pure water, oxygen enhancers, the healthful oral tablets 2 or mini-bars 4 and miscellaneous items is aboard spacecraft for back-up emergency supplies.

The containers 46 of the present invention are also suitable for general use in carrying and storing objects which should be protected from changes in temperature and physical jarring.

While the fundamental novel features of the invention have been pointed out, it will be understood that various omissions and substitutions and changes of the form and detail may be made by those skilled in the art without departing from the spirit of the invention.

The features of the invention in which an exclusive right is claimed are defined as follows:

We claim:

1. A method of preparing a cylindrical body comprising a first end surface, a second end surface, and a edge joining the first and second end surfaces, said body comprising a multiplicity of discrete sections extending from the first end surface to the second end surface, each discrete section comprising a solid, healthful ingredient and a binder, which method comprises: extruding a multiplicity of discrete sections containing a least one healthful ingredient a binder; and sufficient water to allow extrusion; simultaneously extruding a matrix section which fills in the spaces between the discrete sections to form a multi-sectioned cylinder; and notching or scoring the cylinder so as to enable easy cutting into tablets of desirable sizes.

2. A segment comprising a first end surface, a second end surface, and a shaped edge joining the first and second end surfaces, said segment comprising a matrix and a multiplicity of discrete sections extending from the first end surface to the second end surface, each discrete section comprising solid, healthful ingredients and a binder.

3. A method of making a healthful oral tablet which will dissolve in the oral cavity, comprising a first end surface, a second end surface, and a shaped edge joining the first and second end surfaces, said tablet comprising a multiplicity of discrete sections extending from the first end surface to the second end surface, each section comprising solid healthful ingredients and a binder, which method comprises: extruding a multiplicity of discrete sections containing healthful ingredients, a binder, and sufficient water to allow extrusion; simultaneously extruding a matrix section which fills in the spaces between the discrete sections to form a multi-sectioned solid shape; and cutting the solid shape to form tablets of desirable sizes.

4. A healthful oral tablet or mini-bar which will dissolve in the oral cavity, comprising a first end surface, a second end surface, and a shaped edge joining the first and second end surfaces, said tablet or mini-bar comprising a matrix and a multiplicity of discrete sections extending from the first end surface to the second end surface, each section comprising solid healthful ingredients and a binder.

5. The healthful oral tablet or mini-bar of claim 4 which is coated with dehydrated food.

6. The healthful oral tablet of claim 5 which is mounted on a lollipop stick.

7. The healthful oral tablet or mini-bar of claim 4, wherein the healthful ingredients are at least one member selected from the group consisting of an oxygen enhancer, a vitamin, an enzyme, soy protein, and a herb.

8. A combination of a multiplicity of the tablets according to claim 4 and a protective thermal insulating wrapper, wherein the tablets are aligned end surface-to-end surface and the edges are surrounded by a thermal insulating protective wrapper, which protective wrapper comprises an inner shaped piece, an outer shaped piece, and a corrugated piece between the inner and the outer shaped pieces for strength.

9. A combination of a mini-bar according to claim 4 and a protective thermal insulating wrapper, wherein the mini-bar is surrounded by a protective wrapper, which protective wrapper comprises an inner shaped piece, an outer shaped piece, and a corrugated piece between the inner and outer shaped pieces for protection.

* * * * *

UNITED STATES PATENT AND TRADEMARK OFFICE
CERTIFICATE OF CORRECTION

PATENT NO : 6,149,939
DATED : 11/21/00
INVENTOR(S): Strumor et al

It is certified that error appears in the above-identified patent and that said Letters Patent is hereby corrected as shown below:

In Col. 3, line 15, "bum" should be amended to read --burn--.

Signed and Sealed this

First Day of May, 2001

Attest:

NICHOLAS P. GODICI

Attesting Officer

Acting Director of the United States Patent and Trademark Office